(12) United States Patent
Hearn

(10) Patent No.: US 6,872,210 B2
(45) Date of Patent: Mar. 29, 2005

(54) STERNUM FIXATION DEVICE

(76) Inventor: James P. Hearn, 25 N. Avon Dr., Claymont, DE (US) 19703

(*) Notice: Subject to any disclaimer, the term of this patent is extended or adjusted under 35 U.S.C. 154(b) by 165 days.

(21) Appl. No.: 10/073,133

(22) Filed: Feb. 13, 2002

(65) Prior Publication Data
US 2002/0143336 A1 Oct. 3, 2002

Related U.S. Application Data
(60) Provisional application No. 60/270,620, filed on Feb. 23, 2001.

(51) Int. Cl.[7] .............................................. A61B 17/80
(52) U.S. Cl. ........................................................ 606/69
(58) Field of Search .............................. 606/69–73, 54, 606/57, 216–221

(56) References Cited

U.S. PATENT DOCUMENTS

| | | | |
|---|---|---|---|
| 408,080 A | 7/1889 | Carroll | |
| 2,486,303 A | 10/1949 | Longfellow | |
| 3,068,869 A | 12/1962 | Shelden et al. | 128/337 |
| 3,385,299 A | 5/1968 | Le Roy | |
| 4,201,215 A * | 5/1980 | Crossett et al. | 606/216 |
| 4,270,248 A | 6/1981 | Akashi | |
| 4,794,675 A | 1/1989 | Bisconti | |
| 4,852,558 A | 8/1989 | Outerbridge | |
| 5,006,120 A | 4/1991 | Carter | |
| 5,139,498 A | 8/1992 | Astudillo Ley | |
| 5,439,463 A | 8/1995 | Lin | |
| 5,616,142 A | 4/1997 | Yuan et al. | |
| 5,620,444 A | 4/1997 | Assaker | |
| 5,667,507 A | 9/1997 | Corin et al. | |
| 5,672,177 A | 9/1997 | Seldin | |
| 5,704,936 A | 1/1998 | Mazel | |
| 5,707,372 A | 1/1998 | Errico et al. | |
| 5,749,873 A | 5/1998 | Fairley | |
| 5,800,433 A * | 9/1998 | Benzel et al. | 606/61 |
| 5,827,286 A | 10/1998 | Incavo et al. | |
| 5,849,012 A | 12/1998 | Abboudi | |
| 5,928,231 A | 7/1999 | Klein et al. | |
| 5,941,881 A | 8/1999 | Barnes | |
| 5,964,762 A | 10/1999 | Biedermann et al. | |
| 5,964,763 A | 10/1999 | Incavo et al. | |
| 6,007,538 A | 12/1999 | Levin | |
| 6,051,007 A | 4/2000 | Hogendijk et al. | |
| 6,053,915 A | 4/2000 | Bruchmann | 606/54 |
| 6,117,135 A * | 9/2000 | Schlapfer | 606/61 |
| 6,139,316 A | 10/2000 | Sachdeva et al. | |
| 6,200,318 B1 | 3/2001 | Har-Shai et al. | |
| 6,206,828 B1 | 3/2001 | Wright | |
| 6,217,580 B1 | 4/2001 | Levin | |
| 6,355,036 B1 * | 3/2002 | Nakajima | 606/57 |
| 6,623,486 B1 * | 9/2003 | Weaver et al. | 606/69 |
| 6,656,179 B1 * | 12/2003 | Schaefer et al. | 606/61 |

FOREIGN PATENT DOCUMENTS

| | | | |
|---|---|---|---|
| DE | 121383 | 9/1900 | |
| DE | 93 21 544 U1 | 9/1999 | A61B/17/58 |
| FR | 2720623 | 12/1995 | |
| JP | 64-43249 | 2/1989 | |
| JP | 2001-37767 | 2/2001 | A61B/17/58 |
| WO | WO 96/36391 | 11/1996 | |
| WO | WO 98/44850 | 10/1998 | |

* cited by examiner

*Primary Examiner*—Eduardo C. Robert
*Assistant Examiner*—Michael B. Priddy
(74) *Attorney, Agent, or Firm*—Jones Day

(57) ABSTRACT

A sternum fixation device for securing parts of a sternum includes first and second removably associated plates. The first plate has an upper surface and a sternum-contacting surface, and at least one hole passing through both of these surfaces for receiving a fastener head. The second plate has at least one attachment member for fixation to the sternum. A release member holds the first and second plates together, and is movably associated with at least one of the first and second plates such that it may be moved to allow separation of the two parts of the sternum.

28 Claims, 19 Drawing Sheets

STERNUM FIXATION DEVICE

CROSS-REFERENCE TO RELATED APPLICATIONS

The benefit of Provisional Application No. 60/270,620, filed Feb. 23, 2001 is claimed under 35 U.S.C. §119(e).

FIELD OF THE INVENTION

The present invention relates generally to surgical devices, and more particularly, to devices for reapproximating two or more parts of a patient's sternum.

BACKGROUND OF THE INVENTION

Many surgical procedures require two or more parts of a sternum to be reapproximated, or fixed together, such as sternal reconstruction and repair of sternal trauma. In addition, various types of surgical procedures are currently performed to investigate, diagnose, and treat diseases involving tissues or organs located in a patient's thoracic cavity, such as the heart and lungs. These procedures typically require a partial or median sternotomy to gain access to the patient's thoracic cavity. A partial or median sternotomy is a procedure by which a saw or other appropriate cutting instrument is used to make a midline, longitudinal incision along a portion or the entire axial length of the patient's sternum, allowing two opposing sternal halves to be separated laterally. A large opening into the thoracic cavity is thus created, through which a surgeon may directly visualize and operate upon the heart and other thoracic organs, vessels, or tissues. Following the surgical procedure within the thoracic cavity, the two severed sternal halves must be reapproximated.

Sternum fixation has traditionally has been performed using stainless steel wires that are wrapped around or through the sternal halves and then twisted together, so as to compress the two halves together. Other methods of sternum fixation include the use of band or strap assemblies. Such assemblies typically include a locking mechanism, which secures a strap in a closed looped configuration around the sternum halves. While utilization of steel wires and strap assemblies have been widely accepted for sternum fixation, these devices present a number of disadvantages. For example, steel wires are susceptible to breakage, are difficult to maneuver and place around the sternum, and often have sharp ends that can pierce through the surgeon's gloves or fingers. Steel wire and band assemblies also provide insufficient or non-uniform clamping force on the sternal halves, thus resulting in sternal nonunion. The steel wire and band assemblies also provide insufficient clamping forces in all three planar directions, thus leading to healing problems caused by unwanted bone movements leading to raking and rubbing of the surrounding tissue or bone.

Several other techniques of sternal fixation have been developed for reapproximating the sternal halves. One technique uses plates that are located on both sternal halves across the sternotomy and are fixed thereto by means of screws through the bone on either side of the sternotomy. This technique, however, is not optimal because it requires direct fixation of the plates to the bone with screws, making reentry into the thoracic cavity through the sternotomy extremely difficult in case of a medical emergency.

Another technique uses a sternal clamp having a pair of opposed generally J-shaped clamp members which are laterally adjustable relative to one another but can be rigidly joined with a set of machine screws. Similar to the use of plates, discussed above, this technique does not provide quick access to the organs and/or tissues within the patient's thoracic cavity.

Yet another fixation device comprises a pair of hook-shaped clamps that slide together and lock in position with respect to one another using a ratchet assembly. The ratchet assembly provides quickened accesses to the thoracic cavity, but is cumbersome to use and is limited to the hook-shaped clamp members disclosed.

Therefore, it is desirable to provide a sternum fixation device that stabilizes the sternum in all three planar directions, has a fast and easy to use quick-release feature, and works in several different configurations.

SUMMARY OF THE INVENTION

The present invention is directed to a sternum fixation device for securing parts of a sternum. The sternum fixation device includes a first plate and a second plate. The first plate has an upper surface and a sternum-contacting surface, at least one hole passing through the upper and sternum-contacting surfaces for receiving a fastener head of a bone fastener, and a first longitudinal bore defining an axis oriented substantially transversely to the at least one hole. The at least one hole may be threaded to receive a threaded fastener head. The second plate has an upper surface and a sternum-contacting surface, an attachment member for fixation to the sternum, and a second longitudinal bore. The first and second plates are dimensioned to mate with one another such that the first and second longitudinal bores are aligned to receive the release member, and removal of the release member from the first and second longitudinal bores allows separation of the two parts of the sternum. The first and second plates mate with one another such that they cannot rotate with respect to one another about the release member.

According to one aspect of the present invention, the release member is a pin, which may be a single pronged pin. The pin may have a splayed apart tip portion. Alternatively, the release member is a two pronged pin, which may be angled with respect to a mating line between the first and second plates. The release member may also be a cam or quarter-turn fastener, and the first and second plates may be provided with matching sets of ratchet teeth that cooperate with the release member to allow the distance between the first and second plates to be varied.

The attachment member may be a threaded through hole that passes through the second plate upper and sternum-contacting surfaces for receiving a threaded fastener head. To increase pull-out resistance of the fastener, the at least one threaded hole may be angled away from the second plate.

According to another embodiment of the present invention, the attachment member is a hook member for engaging an intercostal space portion of the sternum. Preferably, the attachment member comprises at least two hook members that are spaced apart by an adjustable lateral distance. Alternate embodiments include multiple combinations of fastener and hook-shaped attachment members.

DETAILED DESCRIPTION OF THE PREFERRED EMBODIMENTS

Figure 1:
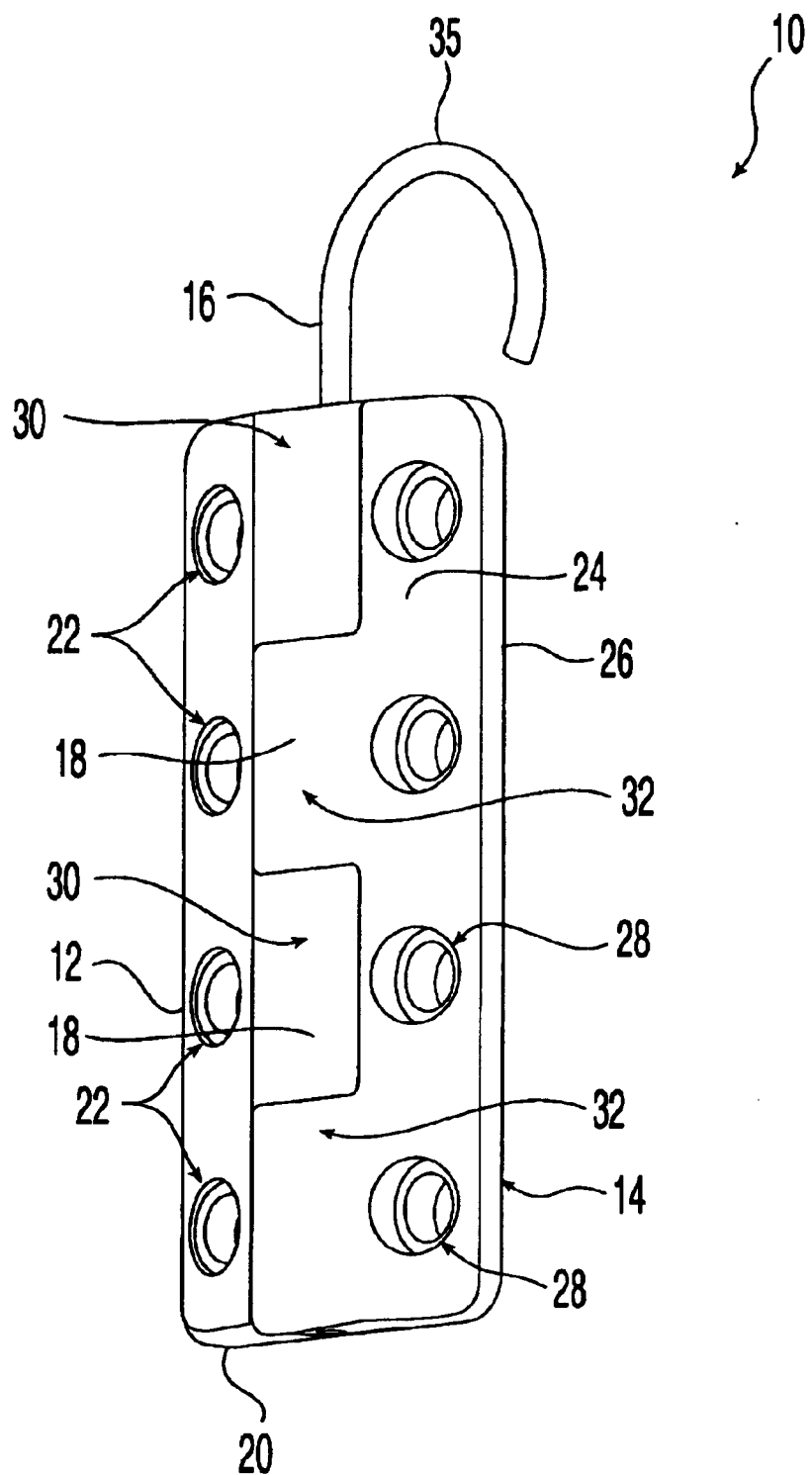
FIG. 1 is a perspective view of a first embodiment of a sternum fixation device according to the present invention.
Figure 2:
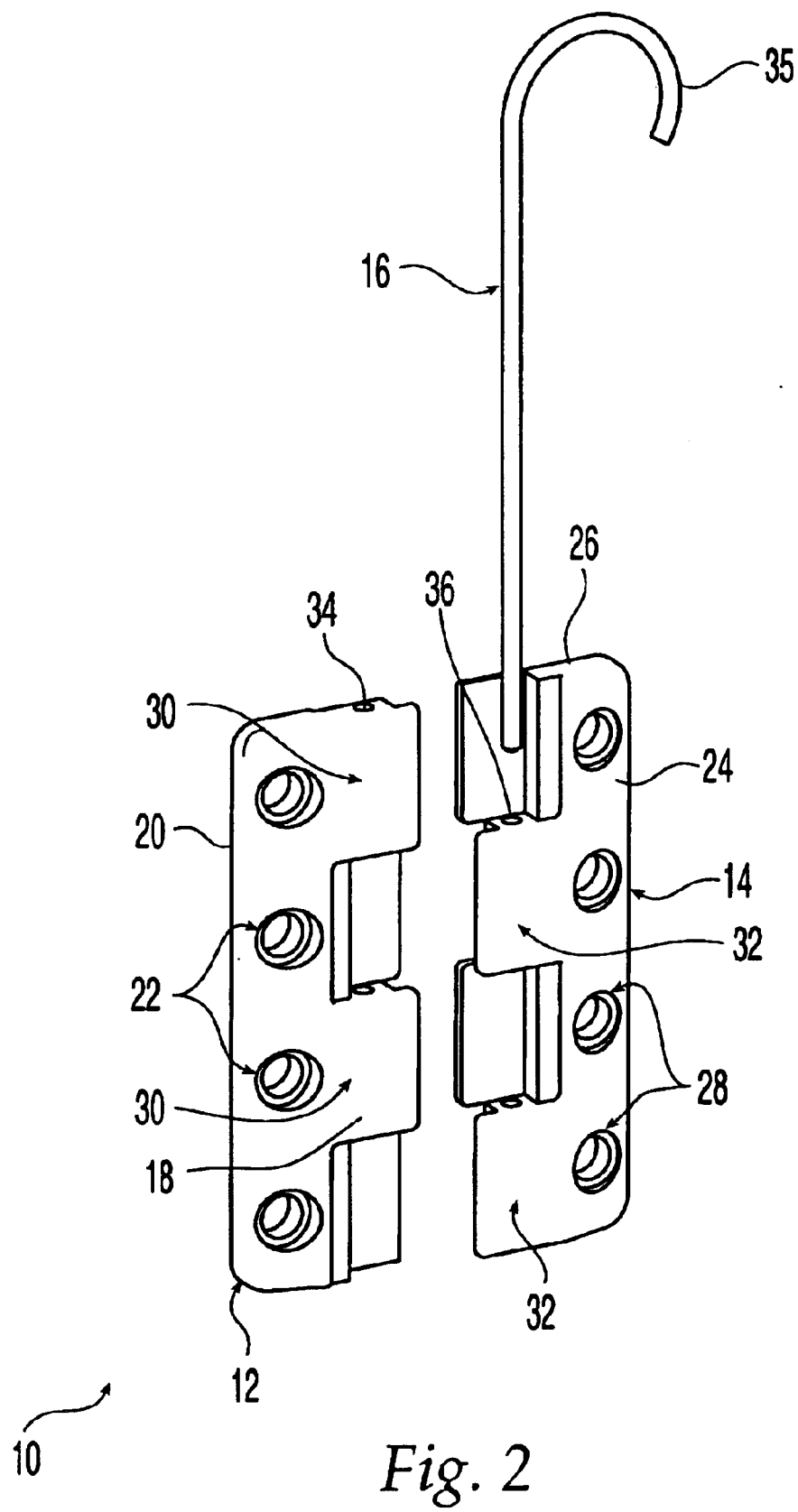
FIG. 2 is an exploded perspective view of the sternum fixation device of FIG. 1.
Figure 19:
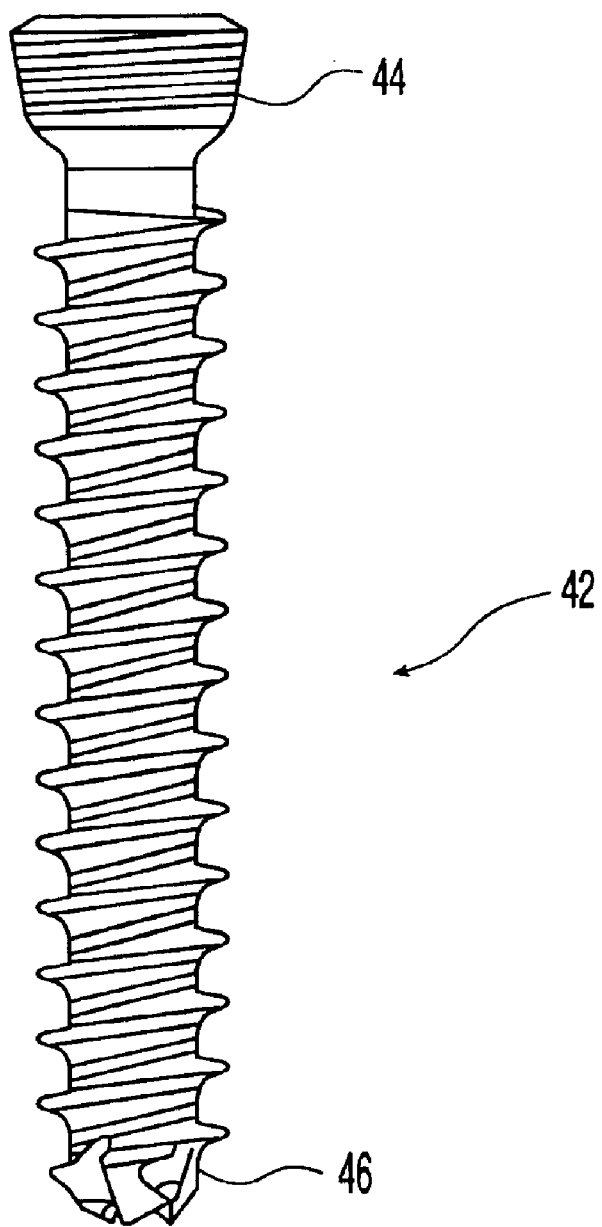
FIG. 19 is an elevational view of a bone fastener having a threaded head portion for use with one embodiment of the first and second attachment members according to the present invention.

FIGS. 1 and 2 show a first illustrative embodiment of a sternum fixation device according to the present invention, shown as sternum fixation device 10. Sternum fixation device 10 includes first and second mating plates 12, 14 attached to one another by a release member 16. First plate 12 and second plate 14 may be used to reapproximate, or secure together, two or more parts of a sternum by attaching each plate to a part of the sternum. Sternum fixation device 10 may be constructed from any suitable bio-compatible material including, but not limited to, bioresorbable materials, radio-translucent materials, allograft materials, stainless steel and titanium First plate 12 includes an upper surface 18 and a sternum-contacting surface 20, and a first attachment member 22 for attachment to the sternum. First attachment member 22 is shown as a plurality of threaded holes that are configured to receive a threaded head portion 44 of a fastener, such as a bone screw 42, shown in FIG. 19. The fastener may alternatively have an elongated shaft with barbs formed thereon that anchor the fastener in the bone. Second plate 14 includes an upper surface 24 and a sternum-contacting surface 26, and a second attachment member 28, also shown as a plurality of threaded holes for receiving a threaded head portion of a bone screw 42. Alternatively, the holes of the first and second attachment members 22, 28 may not have threads and receive a non-threaded head portion of a fastener. Sternum-contacting surfaces 20, 26 may be scalloped, or provided with various other surface treatments that are known by one of ordinary skill in the bone plating art to minimize the contact area between the first and second plates 12, 14 and the respective parts of the sternum.

First plate 12 further includes a series of first joining portions 30 that inter-digitate with corresponding second joining portions 32 on second plate 14. A first longitudinal bore 34 extends through the first joining portions 30 and a second longitudinal bore 36 extends through the second joining portions 32 such that when first plate 12 and second plate 14 are positioned adjacent one another with the first and second joining portions 30, 32 inter-digitated, the first and second longitudinal bores 34, 36 are substantially aligned and may receive release member 16. Alternatively, the first and second joining portions 30, 32 could be provided with multiple sets of aligned longitudinal bores to allow the distance between the first and second attachment members 22, 28 to be varied to accommodate a range of sternum sizes.

As shown in FIGS. 1 and 2, release member 16 is shown as an elongated pin having a curved grip portion 35. Release member 16 could alternatively have a T-shaped grip portion. When inserted into aligned first and second longitudinal bores 34, 36, release member 16 secures the first and second plates 12, 14 together. As shown in FIG. 2, when the release member 16 is removed from the first and second longitudinal bores 34, 36, the first and second plates 12, 14 are allowed to separate. Thus, release member 16 can be removed from the first and second longitudinal bores 34, 36 to quickly and conveniently gain access to the thoracic cavity. This quick release mechanism can be useful, for example, in the case of a medical emergency.

According to one aspect of the present invention, first and second joining portions 30, 32 may be configured such that the first and second plates 12, 14 cannot rotate with respect to one another about the release member 16, thus providing increased stabilization of the two parts of the sternum. As shown in FIG. 2, the first and second joining portions 30, 32 overlap as well as inter-digitate, thus fixing the plates together such that they do not rotate with respect to one another. As an alternative to overlapping the joining portions, release member 16 may be configured to prevent relative rotation between the first and second plates 12, 14. For example, release member 16 and the first and second longitudinal bores 34, 36 may have matching polygonal cross-sections, such as rectangular, square, or triangular, which prevent rotation of either of the plates 12, 14 relative to the release member 16 and consequently, relative to one another. The matching cross-sections may also be ovular. Alternatively, release member 16 may be a multi-pronged pin and the first and second joining portions 30, 32 may be provided with multiple sets of aligned longitudinal bores. One of ordinary skill in the bone plating art, however, will know and appreciate than any number of configurations may be used to prevent rotation between the first and second plates 12, 14.

Figure 3:
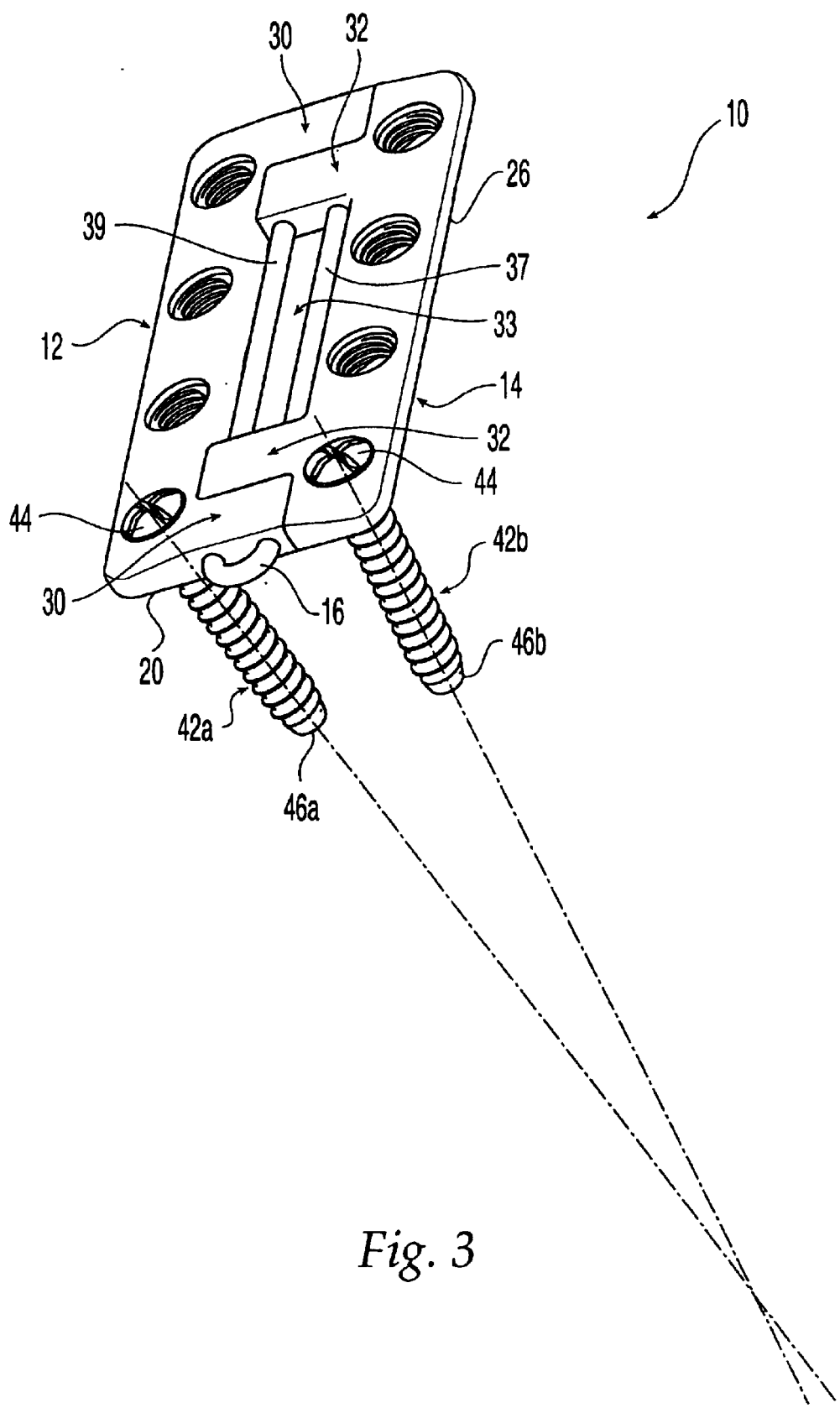
FIG. 3 is a perspective view of the sternum fixation device of FIG. 1, having a U-shaped release member.
Figure 4:
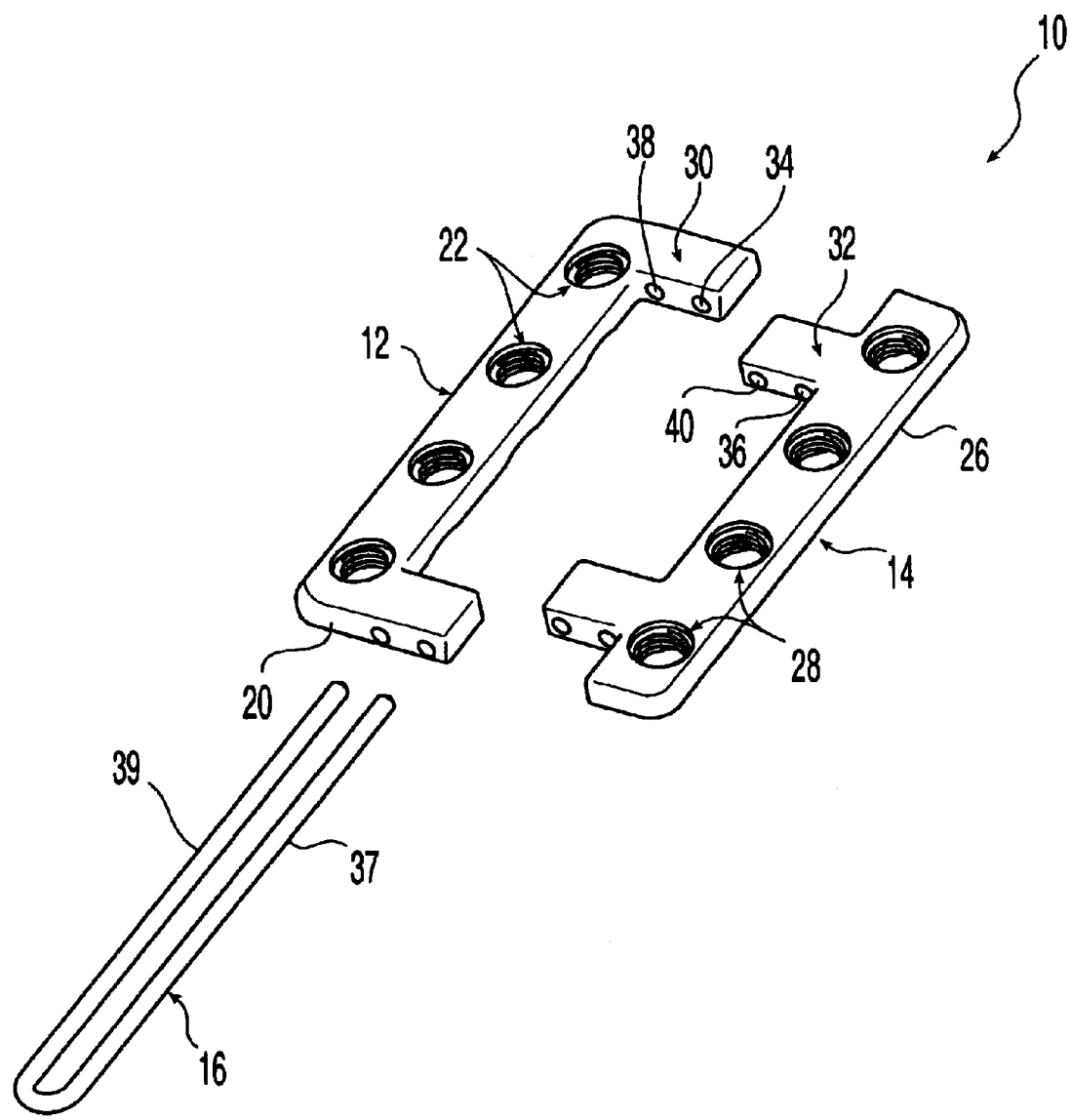
FIG. 4 is an exploded perspective view of the sternum fixation device of FIG. 3.

Referring to FIGS. 3 and 4, a variation of sternum fixation device 10 is shown with release member 16 in the form of a U-shaped pin having spaced apart leg portions 37, 39. The first and second plates 12, 14 have first and second joining portions 30, 32 that are spaced apart such that a central opening 33 is defined between the first and second plates 12, 14. Central opening 33 serves to minimize the amount of implanted material that contacts the sternum. A third longitudinal bore 38 extends through the first mating portion 30 and a fourth longitudinal bore 40 extends through the second mating portion 32. The third and forth longitudinal bores 38, 40 are located such that when the first plate 12 and second plate 14 are positioned adjacent one another with the first and second joining portions 30, 32 inter-digitated, the first and second longitudinal bores 34, 36 are substantially aligned, as are the third and forth longitudinal bores 38, 40. Thus, each of the release member leg portions 37, 39 may be received in one of the aligned pairs of bores to secure the first and second plates 12, 14 together. The spaced apart relationship of leg portions 37, 39 and the respective sets of aligned longitudinal bores prevents the first and second plates 12, 14 from rotating with respect to one another about the release member 16, thus stabilizing the sternum fixation device 10.

Still referring to FIGS. 3 and 4, the first and second attachment members 22, 28 are in the form of a plurality of threaded holes configured to receive a threaded head 44 of a bone screw 42. To reduce the tendency of the bone screws 42 to pull out of the sternum, the threaded holes of the first attachment member 22 and the second attachment member 28 may be angled such that the threaded tip portions 46 of opposing bone screws, for example, bone screws 42a and 42b, are angled towards one another.

Figure 5:
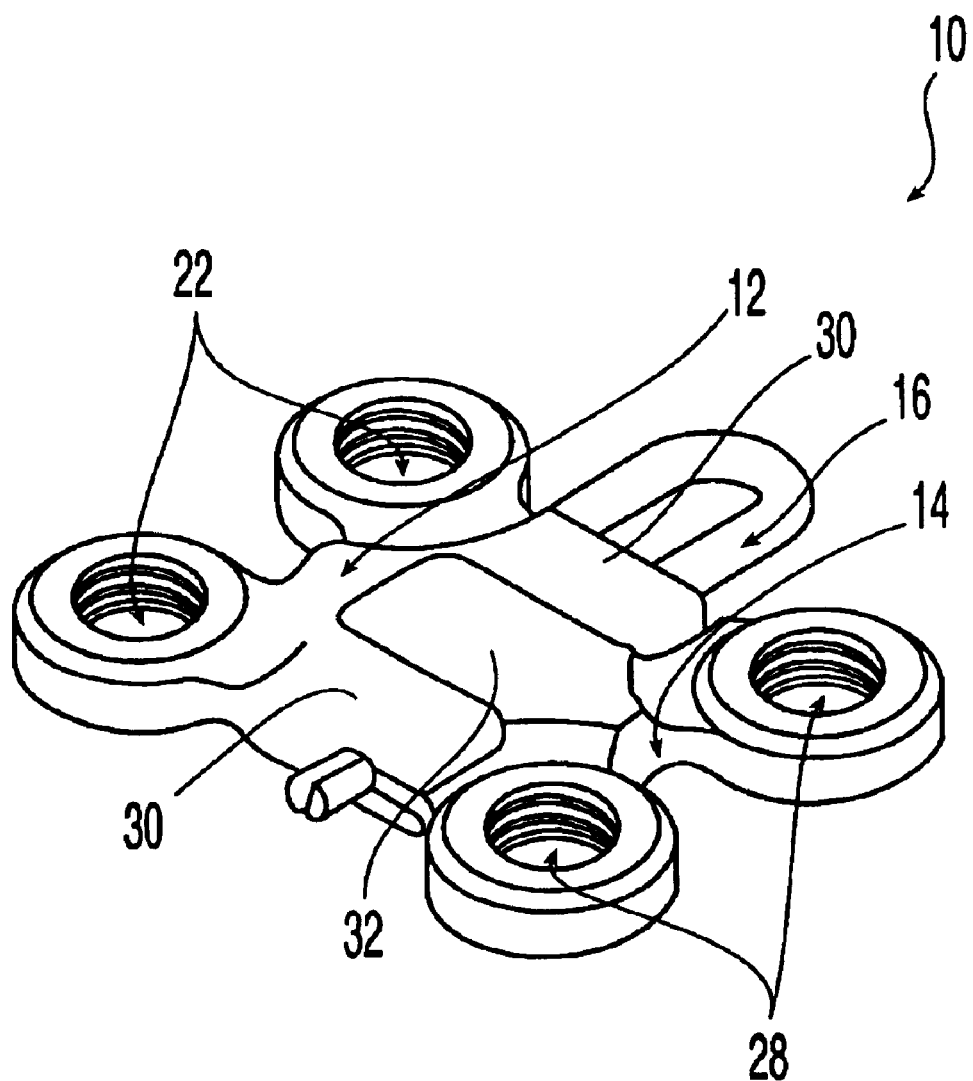
FIG. 5 is a perspective view of the sternum fixation device of FIG. 1, having differently shaped first and second mating portions.
Figure 6:
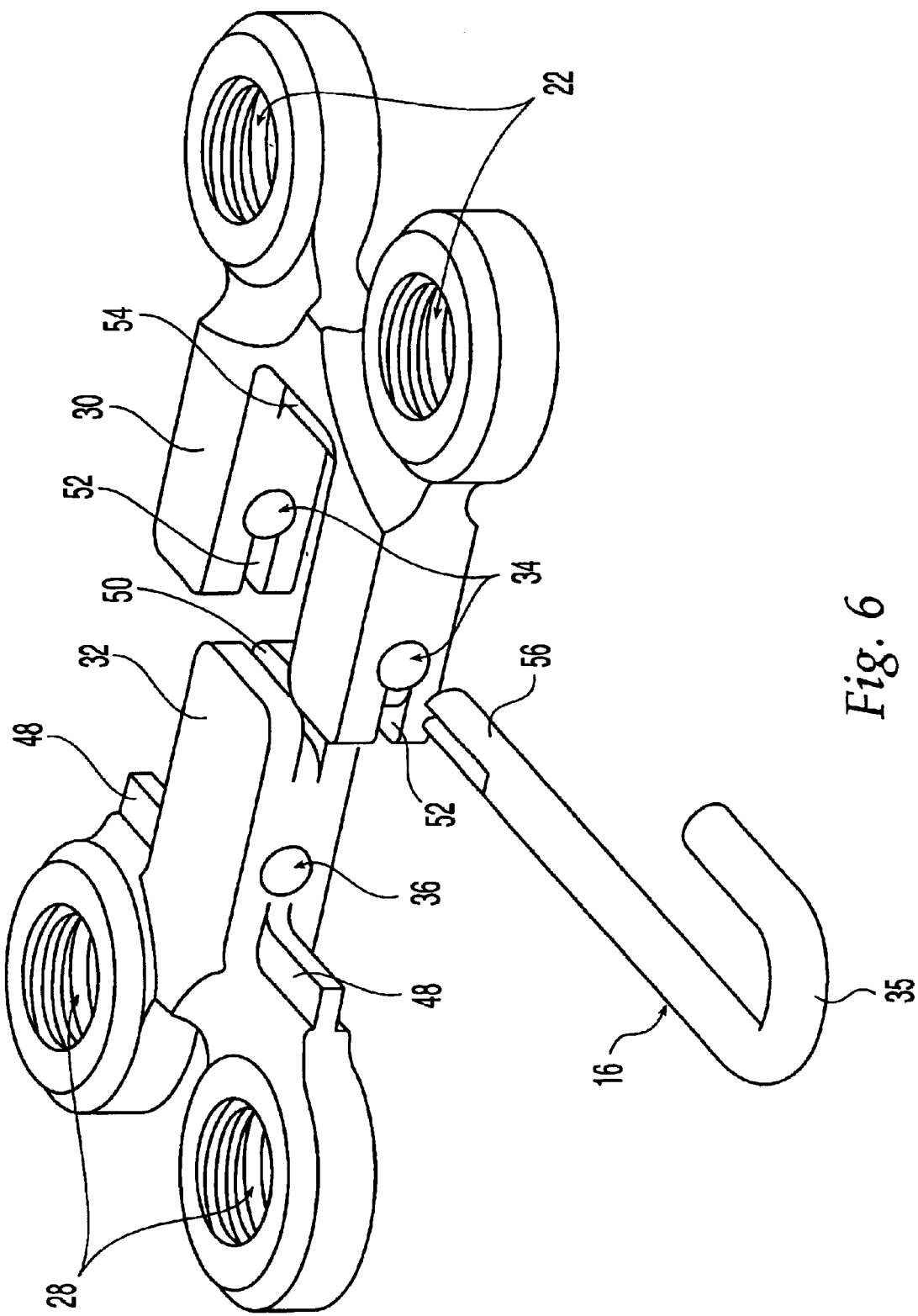
FIGS. 6–7 are exploded perspective views of the sternum fixation device of FIG. 5, showing variations of the first and second mating portions and release member.
Figure 7:
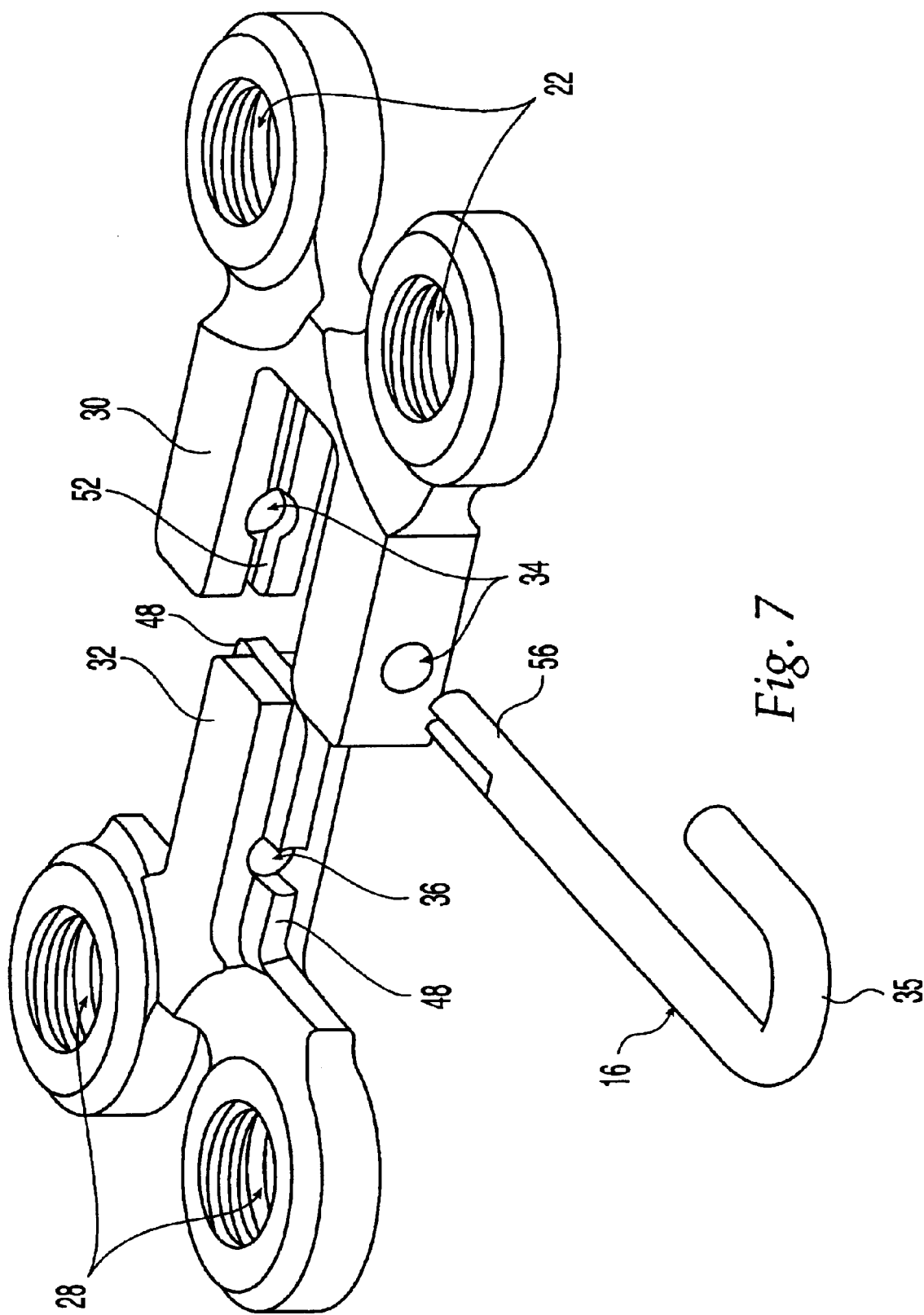

FIGS. 5–12 show several additional variations of sternum fixation device 10. In each of the variations shown, first and second plates 12, 14 are reduced in size so that they outline the first and second attachment members 22, 28, thereby reducing the amount of material that contacts the sternum. Referring to FIGS. 5, 6 and 7, the first and second joining portions 30, 32 may each have protrusions and/or indentations formed thereon to prevent them from rotating with respect to one another. As shown in FIG. 6, second joining portion 32 includes transverse tabs 48 and groove 50, and first joining portion 30 has mating grooves 52 and tab 54 formed thereon, which cooperate to prevent rotation between the first and second plates 12, 14. Release member 16 has a resiliently expanded, or splayed, tip portion 56 that provides resistance against the release member 16 coming out of first and second longitudinal bores 34, 36. Release member 16 may alternatively be a taper pin. As shown in FIG. 7, tabs 48 and grooves 52 may be oriented parallel to the joining portions, however, one of ordinary skill in the bone plating art will know and appreciate that any number of configurations of mating protrusions and/or indentations may be formed on the first and second mating portions 30, 32 to prevent rotation between them.

Figure 8:
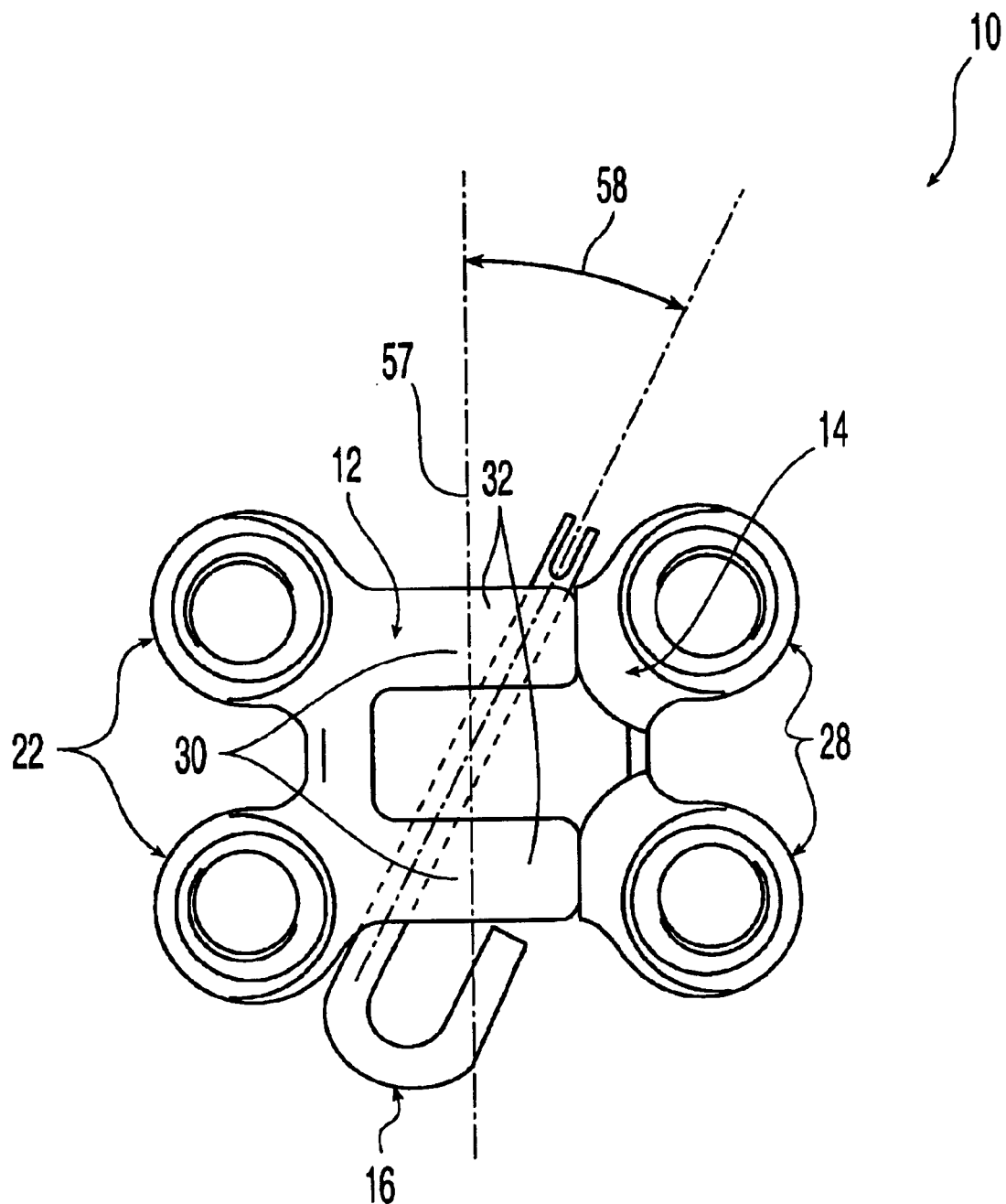
FIG. 8 is an elevational view of the sternum fixation device of FIG. 5, wherein the release member is angled with respect to a mating line between the first and second plates.
Figure 9:
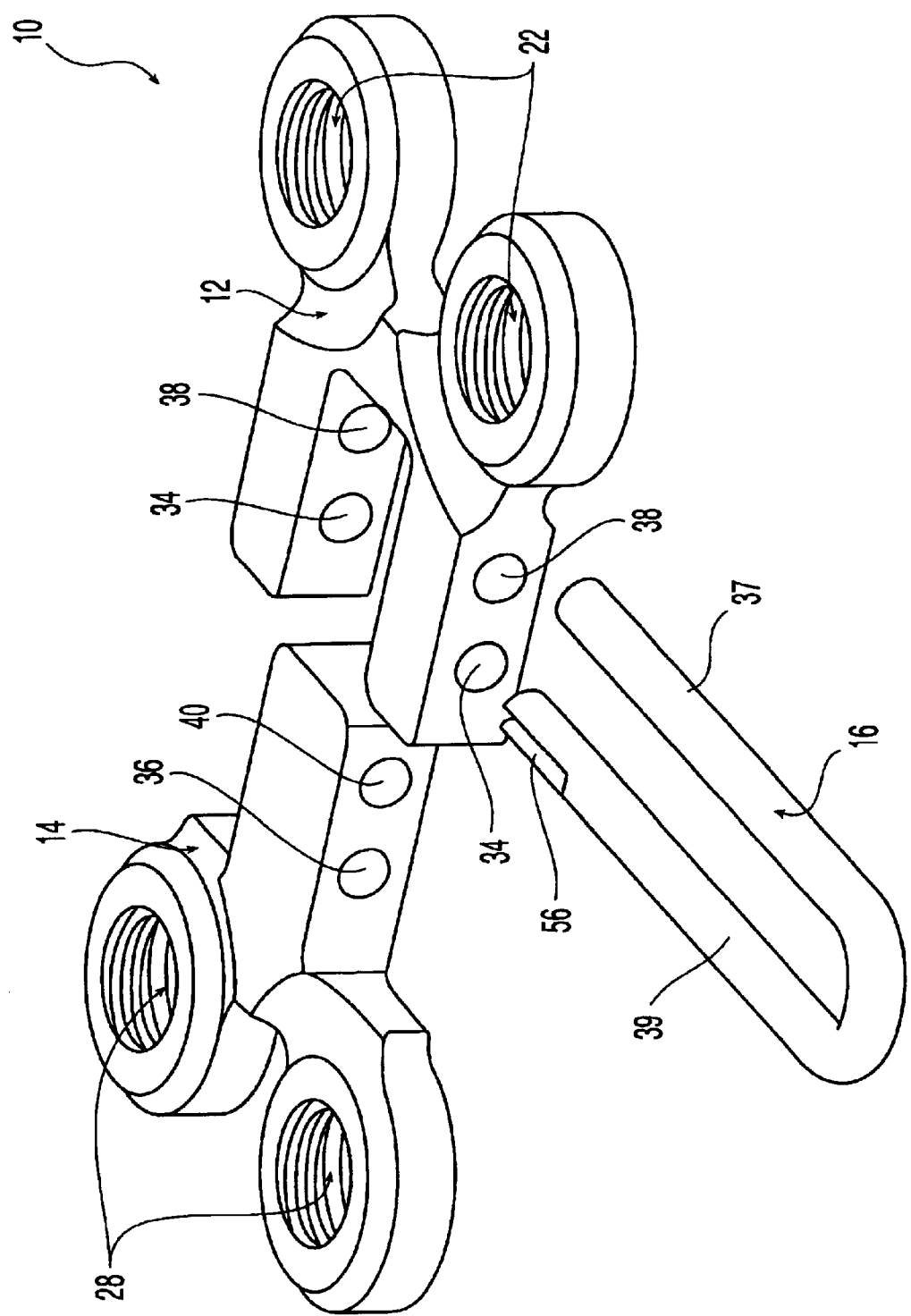
FIG. 9 is a perspective view of the sternum fixation device of FIG. 1, having differently shaped first and second mating portions.
Figure 10:
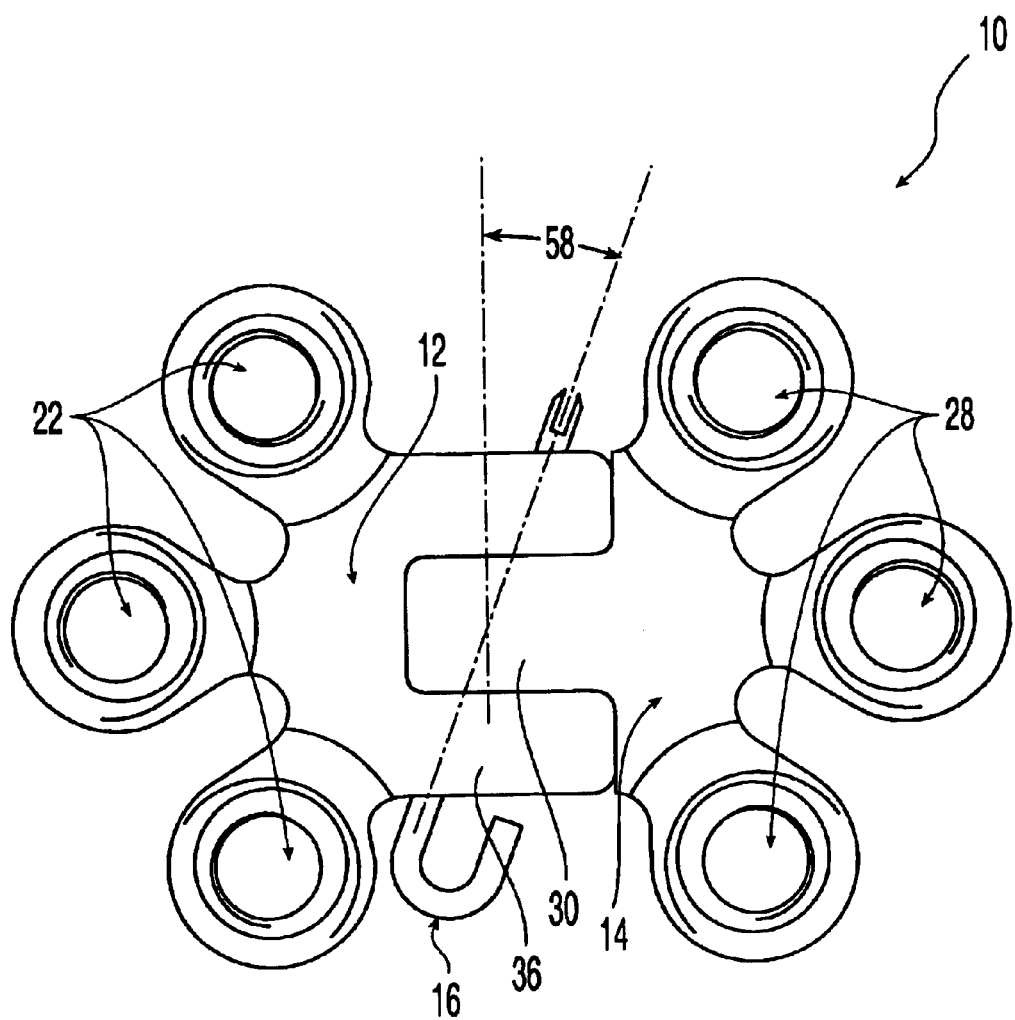
FIGS. 10–12 are elevational views of the sternum fixation device of FIG. 5, having additional first and second attachment members.
Figure 11:
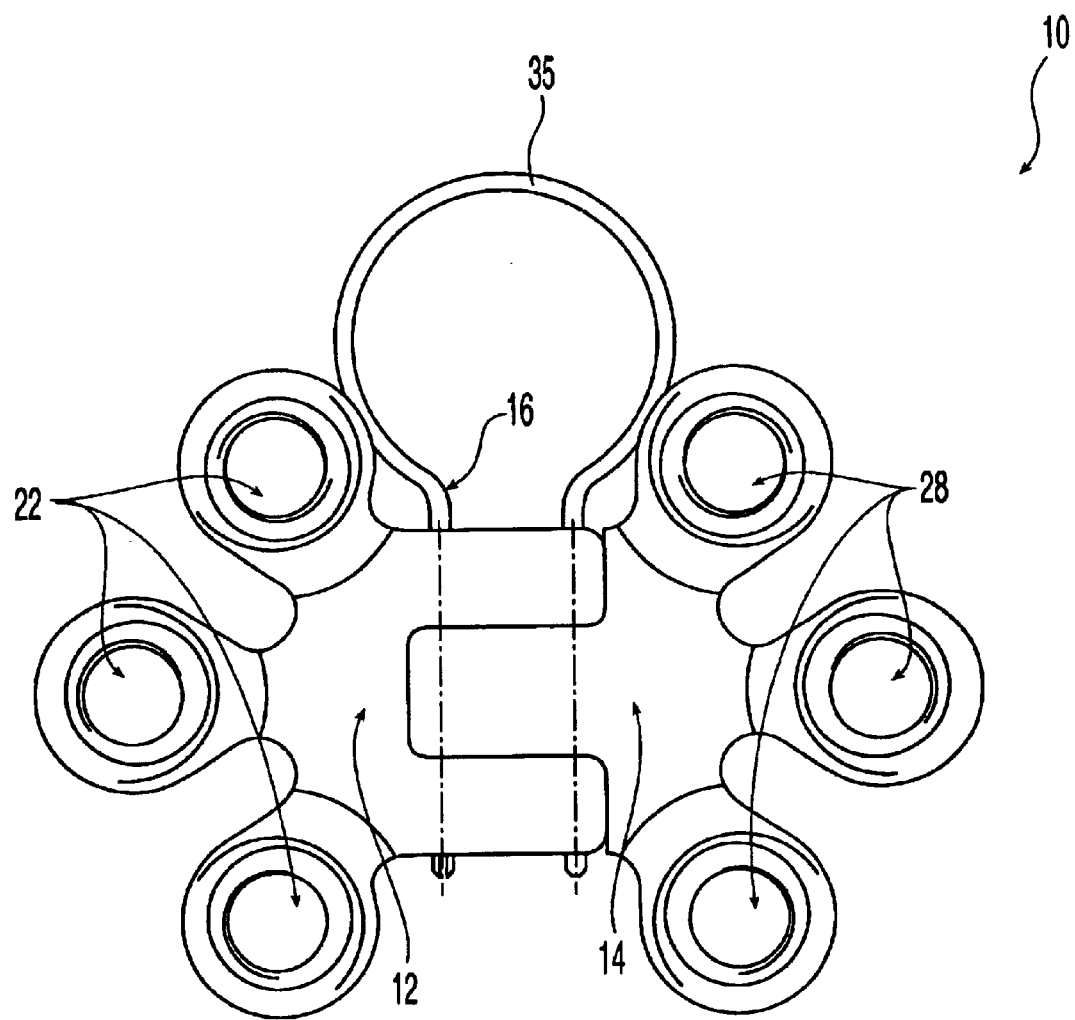
Figure 12:
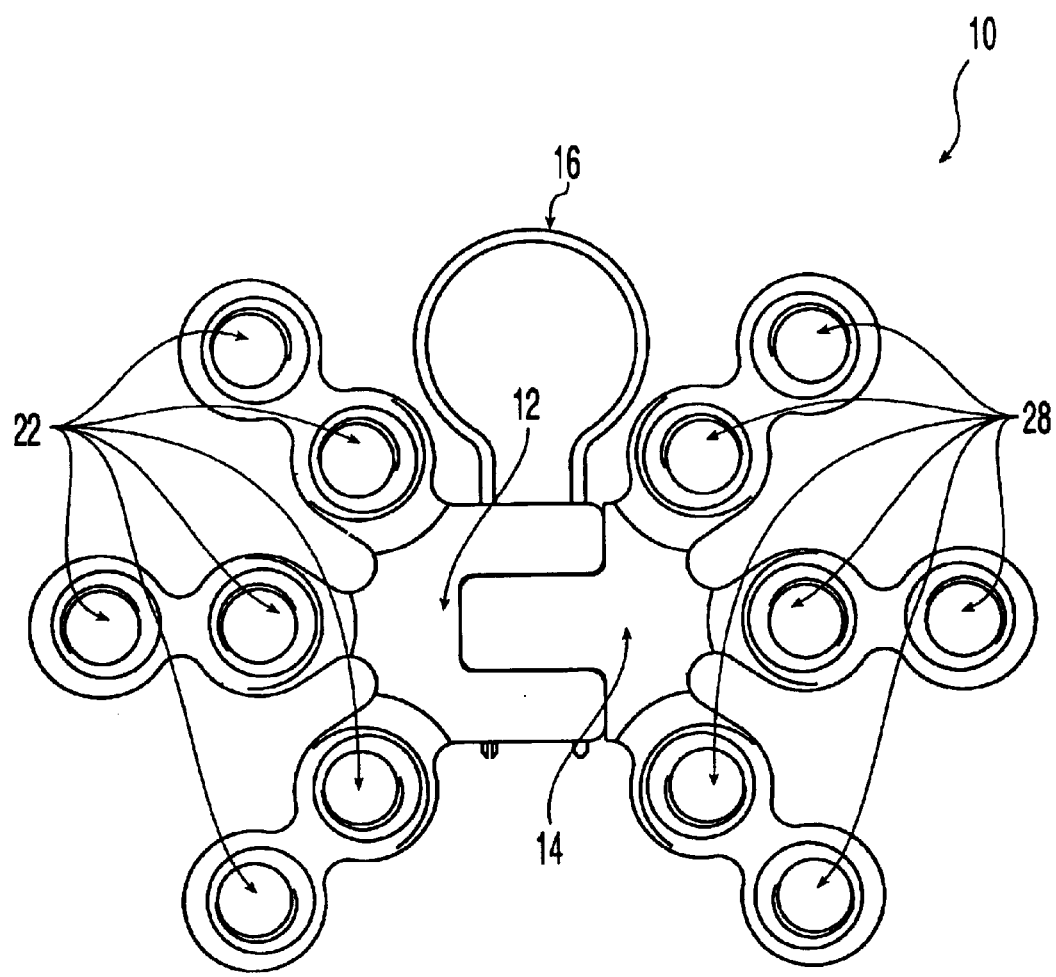
Figure 13:
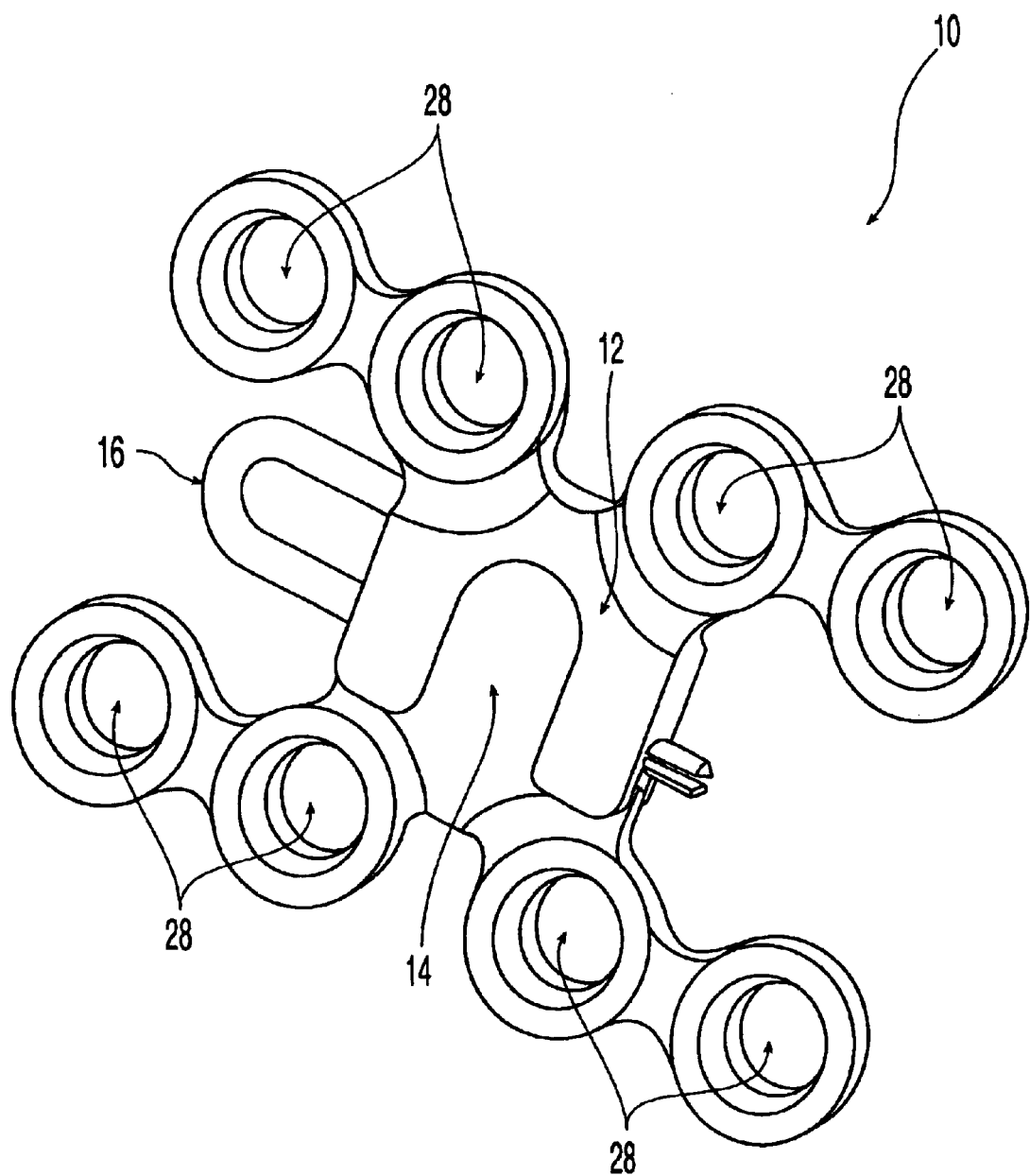
FIG. 13 is a perspective view of the sternum fixation device of FIG. 5, having additional first and second attachment members.

FIG. 8 shows a variation of sternum fixation device 10 wherein the first and second longitudinal bores 34, 36 are oriented at an angle 58 to the intersection 57 of first and second plates 12, 14. When release member 16 is received in aligned first and second longitudinal bores 34, 36 (hidden in FIG. 8), the skewed orientation of release member 16 with respect to intersection 57 prevents rotation between the first and second plates 12, 14. FIG. 9 shows another variation of sternum fixation device 10 having a release member 16 in the form of a U-shaped pin, as discussed above with respect to FIGS. 3 and 4. Release member 16 could alternatively be a V-shaped pin, a T-shaped pin, or any other shape known to one of ordinary skill in the art. FIG. 10 shows a variation of sternum fixation device 10 having first and second attachment members 22, 28 comprising three threaded fastener or screw holes each, and a skewed release member 16. FIG. 11 shows another variation having a U-shaped release member 16 with an enlarged ring-shaped grip portion 35. FIG. 12 shows yet another variation where first attachment member 22 and second attachment member 28 each comprise six threaded fastener or screw holes for receiving a threaded head 44 of a bone fastener or bone screw 42. FIG. 13 shown a variation where the first attachment member 22 and the second attachment member 28 are arranged in a H-shaped pattern. One of ordinary skill in the bone plating art will know and appreciate that any of the features and variations described above may be combined to produce a sternum fixation device according to the present invention.

Figure 14:
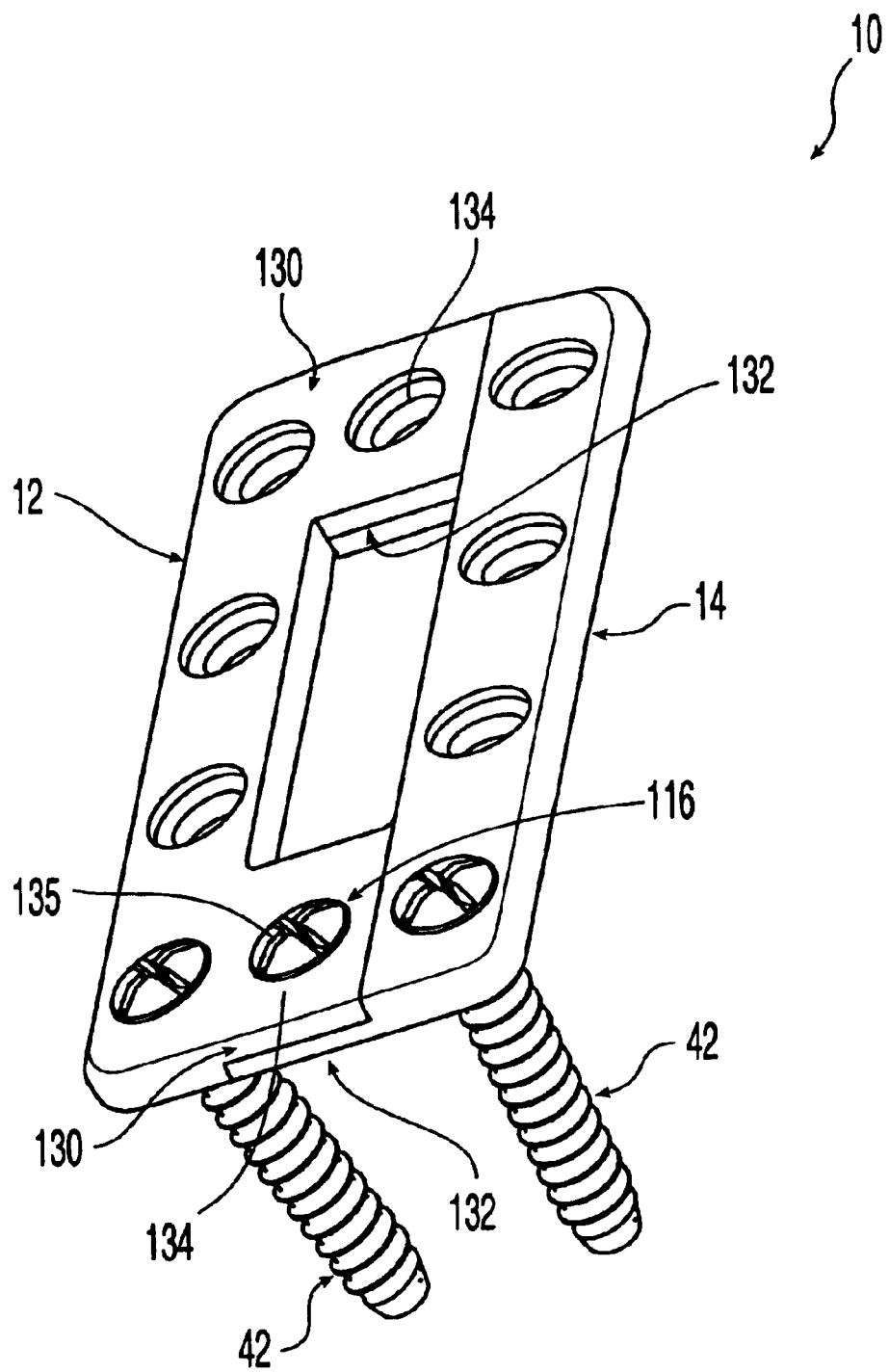
FIG. 14 is a perspective view of a sternum fixation device of FIG. 1, having an alternate embodiment of the release member of FIG. 1.

FIG. 14, shows an alternate embodiment of a release member 116 according to the present invention, which comprises a pair of quarter-turn fasteners or screws, or other cam-type screws known by one of ordinary skill in the art. The first joining portions 130 each have a countersunk bore 134 for receiving a head 135 of the release member 116, and the second joining portions 132 each have a threaded bore, or cam surface 136 (hidden in FIG. 14), for receiving a threaded or cam portion 137 (hidden in FIG. 14) of the release member 116, or vice versa. The first joining portions 130 overlap the second joining portions 132, or vice versa, such that the release member 116 can be inserted through the countersunk bore 134 and be received by cam surface 136 to secure the first and second plates 12, 14 together. To separate the first and second plates 12, 14 the release member 116 is rotated through a predetermined angle preferably of less than 360 degrees, such as, for example ninety degrees, to release the cam portion 137 of the release member 116 from the cam surface 136 and allow the first and second plates 12, 14 to come apart.

Referring to FIGS. 14–17, a second embodiment of the present invention is shown as sternum fixation device 210. Sternum fixation device 210 includes first and second plates 212, 214 attached to one another by release member 216. First plate 212 includes an upper surface 218 and a sternum-contacting surface 220, and first attachment member 222. As will be discussed in more detail below, first attachment member 222 is a plurality of hooks that are configured and dimensioned to engage the sternum between the intercostal spaces. Second plate 214 includes an upper surface 224 and a sternum-contacting surface 226, and second attachment member 228. Second attachment member 228 is a plurality of holes for receiving a bone fastener or screw 242, which holes are preferably threaded to receive a threaded head 244 of the bone screw 242.

Figure 15:
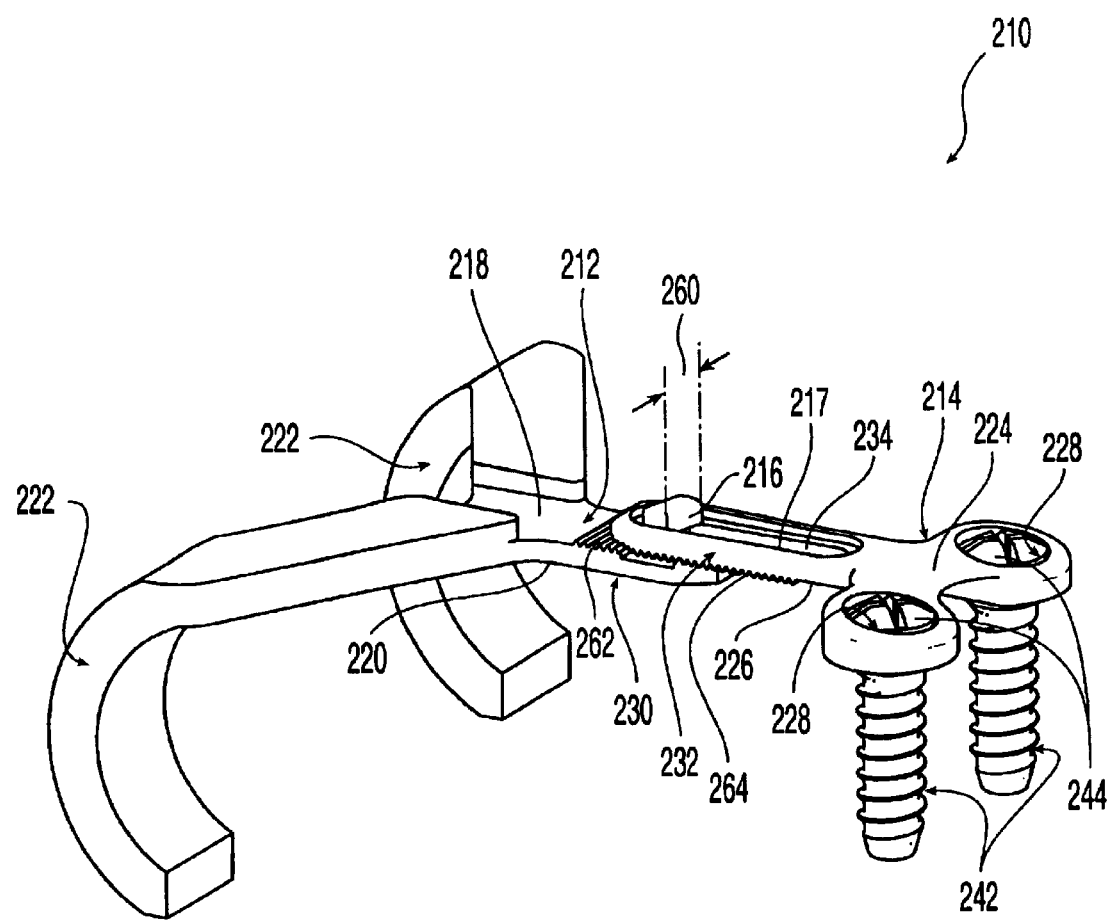
FIG. 15 is a perspective view of a second embodiment of a sternum fixation device according to the present invention, having hook-shaped attachment members.
Figure 16:
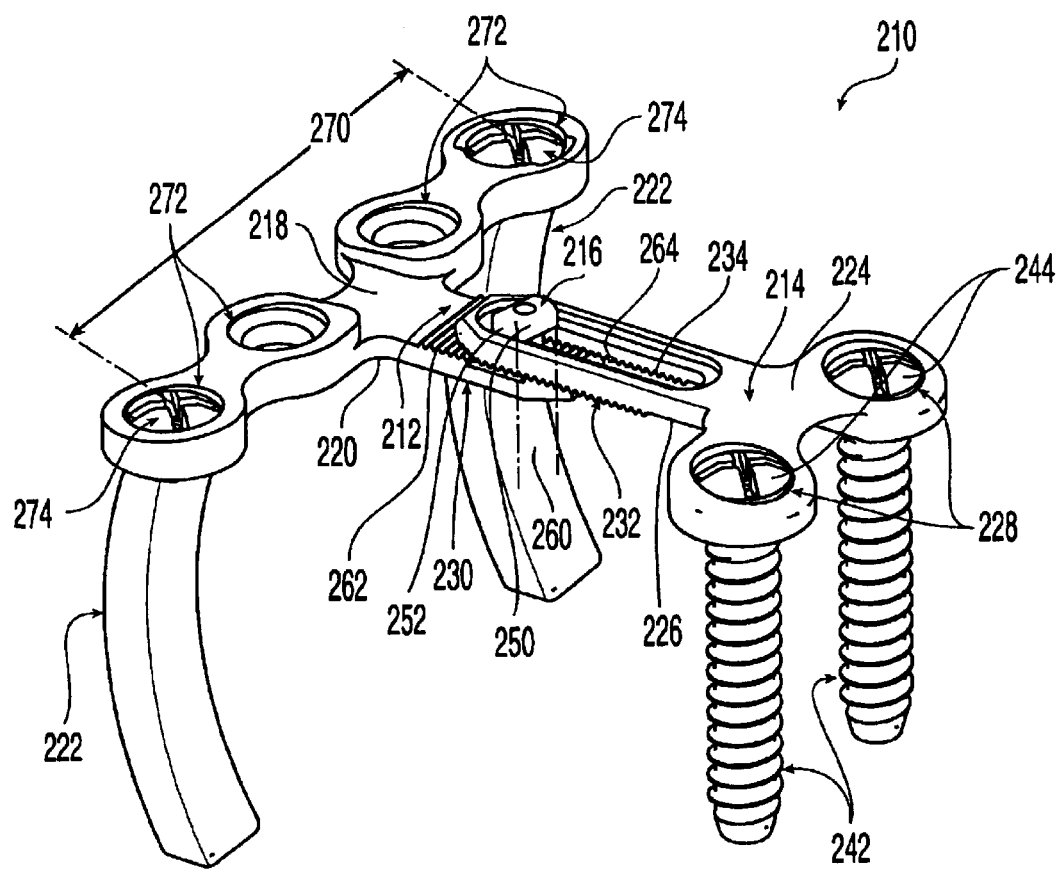
FIG. 16 is a perspective view of the sternum fixation device of FIG. 15, having adjustably spaced-apart hook members.

First plate 212 further includes a first joining portion 230 that overlaps with corresponding second joining portion 232 on second plate 214. An elongated slot 234 extends through the second joining portion 232 and is dimensioned to receive release member 216, which is a cam, as shown in FIGS. 14 and 15, or quarter-turn fastener or screw, as shown in FIG. 16. As shown in FIGS. 14 and 15, release member 216 may be a generally rectangular cam that is rotatable between a locking position and a releasing position and has a first dimension 260 that can pass through the slot 234 when it is oriented parallel thereto, but can not pass through the slot 234 when it is substantially transverse thereto. Thus, when release member 216 is in the locking position, the first dimension 260 is oriented substantially transverse to the elongated slot 234 and locks the first and second plates 212, 214 together. When release member 216 is rotated into the releasing position, the first dimension 260 is in alignment with the elongated slot 234 and allows separation of the first and second plates. FIG. 16 shows release member 216 as a quarter-turn screw having a head 235 and a threaded portion 237 (hidden). Threaded portion 237 passes through elongated slot 234 and engages a threaded bore 236 (hidden) in first joining portion 230, and head 235 engages the upper surface 224 of second joining portion 232 to lock the first and second plates 212, 214 together. According to either configuration of release member 216, cam or quarter-turn screw, the first and second plates 212, 214 may be separated by rotating release member 216 through a predetermined angle preferably of less than 360 degrees, such as, for example, ninety degrees, to free release member 216 from elongated slot 234 and allow the first and second plates 212, 214 to separate. One of ordinary skill in the art will know and appreciate that any number of cam or quarter-turn screw configurations may be used to releasably lock the first and second plates 212, 214 together.

Referring to FIGS. 14–16, first and second joining portions 230, 232 may each have a series of transverse ratchet teeth 262, 264 defined thereon that cooperate to lock first and second plates 212, 214 together. The position of second joining portion 232 may be varied incrementally with respect to first joining portion 232, provided that release member 216 is maintained within the boundaries of elongated slot 234, which position may be locked by the cooperation of transverse ratchet teeth 262, 264, which are pressed together by release member 216. Thus, first and second plates 212, 214 can be locked together at varying distances apart from one another, allowing sternum fixation device 210 to be used with sternums of different sizes.

Figure 18:
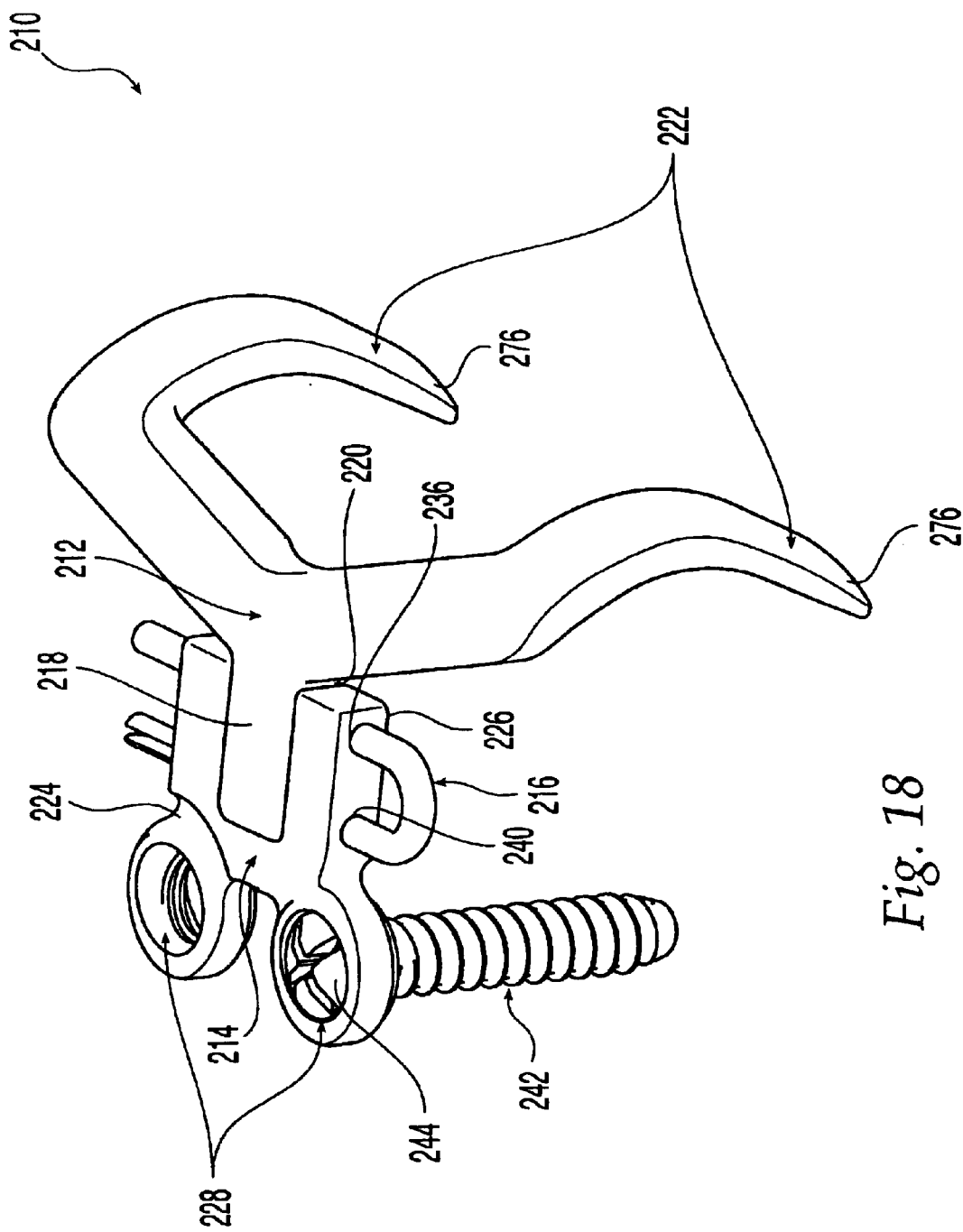
FIG. 18 is a perspective view of the sternum fixation device of FIG. 15, having an alternate embodiment of the release member.

FIG. 18 shows a variation of sternum fixation device 210 where release member 216 is a U-shaped pin that is received in sets of substantially aligned longitudinal bores 234 (hidden), 236 and 238 (hidden), 240 disposed in interdigitated first and second joining portions 230, 232, as described above with respect to sternum fixation device 10. One of ordinary skill in the art will appreciate that all the configurations of the release member 16 and the first and second joining portions 30, 32, as described above with respect to sternum fixation device 10, may also be used with sternum fixation device 210.

Figure 17:
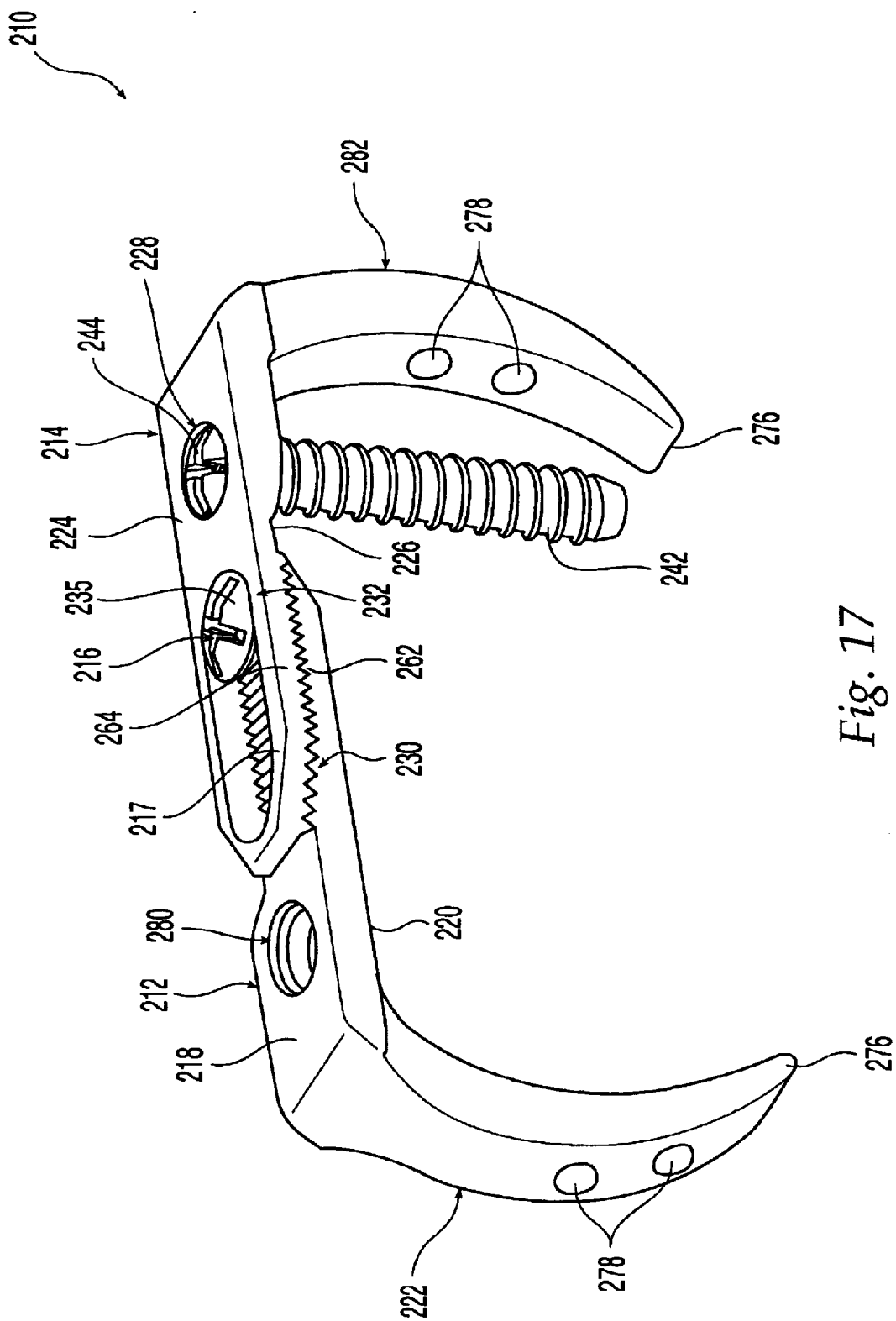
FIG. 17 is a perspective view of the sternum fixation device of FIG. 15, having first and second attachment members including a combination of hooks and threaded fastener holes.

Referring back to FIG. 15, first attachment member 222 is shown as a pair of laterally spaced-apart, generally curved hooks for engaging the intercostal spaces of a patient's sternum. First attachment member 222 may have C-shaped, J-shaped, L-shaped, or any other shaped hooks known in the art to be suitable for engaging the intercostal spaces of a sternum. One of ordinary skill in the art will appreciate that first attachment member 222 may have any number of hooks configured for engaging any respective number of intercostal spaces. In addition, first attachment member 222 can be made having various different dimensions, such as the size of the hooks and the lateral spacing therebetween, to accommodate sternums having different sizes and proportions. FIG. 16 shows a variation of first attachment member 222 where the number of hooks 270 and the lateral distance between them is adjustable. First plate 212 has a longitudinal array of mounting apertures 272 defined therein for receiving mounting bolts 274 that secure the hooks to the first plate 212, thus allowing the mounting position of the hooks to be adapted to conform to varying distances between intercostal spaces. Mounting bolts 274 are preferably recessed into mounting apertures 272, for example, by countersinking or counterboring the apertures 272, to reduce the amount of material protruding above upper surface 218. Referring to FIGS. 17 and 18, the first attachment member 222 can have pointed, self-dissecting tip portions 276 that aid in inserting the hooks through soft tissue and muscle that is found in the intercostal spaces. First attachment member 222 can additionally have apertures 278 (shown in FIG. 17) defined therein for receiving pins that may be used to stabilize attachment member 222 in the intercostal space.

While it is apparent that the illustrative embodiments of the invention herein disclosed fulfil the objectives stated above, it will be appreciated that numerous modifications and other embodiments may be devised by those skilled in the art. For example, as shown in FIG. 17, sternum fixation device 210 may further include third attachment member 280, a threaded hole for receiving a threaded head portion 244 of a bone fastener or screw 242, and fourth attachment member 282, an intercostal space hook. One of ordinary skill in the art will appreciate that sternum fixation device 210 may include any number and combination of attachment members, such as hooks and bone screws, and release members, such as pins, U-shaped pins, and cam members. Therefore, it will be understood that the appended claims are intended to cover all such modifications and embodiments which come within the spirit and scope of the present invention.

What is claimed is:

1. A sternum fixation device for securing parts of a sternum comprising:
   a first plate having an upper surface and a sternum-contacting surface, and at least one hole passing through the upper and sternum-contacting surfaces for receiving a fastener head, the first plate further including a first longitudinal bore defining an axis oriented substantially transversely to the at least one hole;
   a second plate having an upper surface and a sternum-contacting surface, and an attachment member for fixation to the sternum, the second plate further including a second longitudinal bore; and
   a removable release member for holding the first and second plates together, wherein the first and second plates are dimensioned to releasably mate with one another such that the first and second longitudinal bores are aligned to receive the release member;
   wherein the release member is a pin that is substantially U-shaped or T-shaped.

2. A sternum fixation device for securing parts of a sternum comprising:
   a first plate having an upper surface and a sternum-contacting surface, and at least one hole threaded to receive a threaded fastener head and passing through the upper and sternum-contacting surfaces for receiving a fastener head, the first plate further including a first longitudinal bore defining an axis oriented substantially transversely to the at least one hole;
   a second plate having an upper surface and a sternum-contacting surface, and an attachment member for fixation to the sternum, the second plate further including a second longitudinal bore; and
   a removable release member for holding the first and second plates together, wherein the first and second plates are dimensioned to releasably mate with one another such that the first and second longitudinal bores are aligned to receive the release member; and
   a bone fastener having a threaded fastener head and a shaft and defining a longitudinal axis that extends away from the upper surface toward the sternum-contacting surface, wherein the at least one hole is angled such that when the threaded fastener head is received in the hole, the longitudinal axis is angled toward the second plate.

3. The sternum fixation device of claim 2, wherein the attachment member is a through hole passing through the second plate upper and sternum-contacting surfaces.

4. The sternum fixation device of claim 3, wherein the through hole is threaded to receive a threaded fastener head.

5. The sternum fixation device of claim 2, wherein the first and second plates mate at a mating line, and at least one of the first and second longitudinal bores is disposed at an angle with respect to the mating line.

6. A sternum fixation device for securing parts of a sternum comprising:
   a first plate having an upper surface and a sternum-contacting surface, and at least one hole passing through the upper and sternum-contacting surfaces for receiving a fastener head, the first plate further including a first longitudinal bore defining an axis oriented substantially transversely to the at least one hole;
   a second plate having an upper surface and a sternum-contacting surface, and an attachment member for fixation to the sternum, the second plate further including a second longitudinal bore; and
   a removable release member for holding the first and second plates together, wherein the first and second plates are dimensioned to releasably mate with one another such that the first and second longitudinal bores are aligned to receive the release member;
   wherein the attachment member is a hook member for engaging an intercostal space portion of the sternum.

7. A sternum fixation device for securing parts of a sternum comprising:
   a first plate having an upper surface and a sternum-contacting surface, and at least one hole passing through the upper and sternum-contacting surfaces for receiving a fastener head, the first plate further including a first longitudinal bore defining an axis oriented substantially transversely to the at least one hole;
   a second plate having an upper surface and a sternum-contacting surface, and an attachment member for fixation to the sternum, the second plate further including a second longitudinal bore; and
   a removable release member for holding the first and second plates together, wherein the first and second plates are dimensioned to releasably mate with one another such that the first and second longitudinal bores are aligned to receive the release member;
   wherein the first and second plates mate with one another such that they cannot rotate with respect to one another about the release member.

8. The sternum fixation device of claim 7, wherein the attachment member is a through hole passing through the second plate upper and sternum-contacting surfaces.

9. The sternum fixation device of claim 8, wherein the through hole is threaded to receive a threaded fastener head.

10. The sternum fixation device of claim 7, wherein the first and second plates mate at a mating line, and at least one of the first and second longitudinal bores is disposed at an angle with respect to the mating line.

11. A sternum fixation device for securing parts of a sternum comprising:
    a first plate having an upper surface and a sternum-contacting surface, and at least one hole passing through the upper and sternum-contacting surfaces for receiving a fastener head, the first plate further including a first longitudinal bore defining an axis oriented substantially transversely to the at least one hole;
    a second plate having an upper surface and a sternum-contacting surface, and an attachment member for fixation to the sternum, the second plate further including a second longitudinal bore; and
    a removable release member for holding the first and second plates together, wherein the first and second plates are dimensioned to releasably mate with one another such that the first and second longitudinal bores are aligned to receive the release member;
    wherein the release member is a pin having a tip portion with a plurality of splayed apart fingers.

12. A sternum fixation device for securing parts of a sternum comprising:
    a first plate having an upper surface and a sternum-contacting surface, and at least one hole passing through the upper and sternum-contacting surfaces for receiving a fastener head, the first plate further including a first longitudinal bore defining an axis oriented substantially transversely to the at least one hole;
    a second plate having an upper surface and a sternum-contacting surface, and an attachment member for fixation to the sternum, the second plate further including a second longitudinal bore; and
    a removable release member for holding the first and second plates together, wherein the first and second plates are dimensioned to releasably mate with one another such that the first and second longitudinal bores are aligned to receive the release member;
    wherein the release member is a taper pin.

13. A sternum fixation device for securing parts of a sternum comprising:
    a first plate having an upper surface and a sternum-contacting surface, and at least one hole passing through the upper and sternum-contacting surfaces for receiving a fastener head, the first plate further including a first longitudinal bore defining an axis oriented substantially transversely to the at least one hole and at least one additional first longitudinal bore having an axis substantially parallel to the first longitudinal bore axis;
    a second plate having an upper surface and a sternum-contacting surface, and an attachment member for fixation to the sternum, the second plate further including a second longitudinal bore and at least one additional second longitudinal bore; and
    a removable pin having first and second spaced apart legs, and for holding the first and second plates together, wherein the first and second plates are dimensioned to releasably mate with one another such that the first and second longitudinal bores are aligned to receive the pin;
    wherein when the first and second plates are mated with one another, one of the first and second longitudinal bores are aligned to receive the first leg and another one of the first and second longitudinal bores are aligned to receive the second leg.

14. A sternum fixation device for securing parts of a sternum comprising:
    a first plate having an upper surface and a sternum-contacting surface, and at least one hole passing through the upper and sternum-contacting surfaces for receiving a fastener;
    a second plate having at least one hook member for fixation to the sternum; and
    a release member for holding the first and second plates together, wherein the release member is slidably associated with both the first and second plates such that it may be moved to allow separation of the two parts of the sternum.

15. The sternum fixation device of claim 14, wherein the first plate further includes at least one first longitudinal bore defining an axis oriented substantially transversely to the at least one through hole, and the second plate further includes at least one second longitudinal bore, and the first and second plates are dimensioned to mate with one another such that at least the first and second longitudinal bores are aligned to receive the release member such that removal of the release member from the first and second longitudinal bores allows separation of the two parts of the sternum.

16. The sternum fixation device of claim 14, wherein at least one fastener is a bone screw.

17. The sternum fixation device of claim 16, wherein at least one bone screw is self-drilling.

18. The sternum fixation device of claim 16, wherein at least one bone screw is self-tapping.

19. The sternum fixation device of claim 14, wherein the at least one hole is threaded.

20. A method for securing parts of a sternum, comprising the steps of:
   (a) providing a first plate with at least one hole for receiving a fastener, and a second plate with at least one hook member;
   (b) contacting at least one hook member with a first part of the sternum;
   (c) inserting at least one fastener through the hole in the first plate and into a second part of the sternum; and
   (d) linking the first and second plates with a removable release member, wherein the first and second plates are separable upon the removal of the release member.

21. The method of claim 20, wherein steps (b) and (c) are reversed.

22. The method of claim 20, further comprising the step (e) of removing the release member.

23. The method of claim 20, wherein the fastener is a bone screw.

24. The method of claim 20, wherein the at least one hole is threaded.

25. The method of claim 20, wherein the release member is slidably associated with both the first and second plates.

26. The method of claim 20, wherein the first part of sternum is the intercostal space portion of the sternum.

27. The method of claim 20, wherein the first and second plates are linked such that they cannot rotate with respect to one another about the release member.

28. The method of claim 20, wherein the release member is a pin.

* * * * *